United States Patent [19]

Zoeke et al.

[11] 4,334,955

[45] Jun. 15, 1982

[54] DEVICE FOR CONTROLLING EVAPORATION OF A LIQUID

[75] Inventors: Siegfried Zoeke, Munich; Anton Stuerzer, Grafing, both of Fed. Rep. of Germany

[73] Assignee: Siemens Aktiengesellschaft, Berlin & Munich, Fed. Rep. of Germany

[21] Appl. No.: 183,945

[22] Filed: Sep. 4, 1980

[30] Foreign Application Priority Data

Sep. 12, 1979 [DE] Fed. Rep. of Germany ....... 2936895

[51] Int. Cl.³ ............................................... B01D 1/02
[52] U.S. Cl. ..................................... 159/44; 219/518; 200/85 R
[58] Field of Search .................... 219/518, 271–273, 219/275, 452, 433, 362; 200/85 R; 155/44

[56] References Cited

U.S. PATENT DOCUMENTS

| | | | |
|---|---|---|---|
| 693,650 | 2/1902 | Johnson | 200/85 R |
| 2,166,728 | 7/1939 | Page | 219/518 |
| 2,617,005 | 11/1952 | Jorgensen | 219/518 |

FOREIGN PATENT DOCUMENTS 804609 11/1958 United Kingdom ............... 219/518

*Primary Examiner*—Norman Yudkoff
*Attorney, Agent, or Firm*—Hill, Van Santen, Steadman, Chiara & Simpson

[57] ABSTRACT

A device for controlling evaporation of a liquid has a container and a heating element for heating and evaporating liquid in the container. The container is disposed on a base plate which is supported by a leaf spring which allows the base plate to move between two microswitches depending upon the amount of liquid in the container. The microswitches are connected to a control circuit for activating the heating element and interrupt the flow of power to the heating element when little or no liquid is present in the container, or when a maximum amount of liquid is present in the container.

3 Claims, 3 Drawing Figures

DEVICE FOR CONTROLLING EVAPORATION OF A LIQUID

BACKGROUND OF THE INVENTION

The present invention relates to a device for controlling evaporation of a liquid, and in particular to such a device having a container for receiving the liquid and a heating element for heating the liquid and a base plate movable between two microswitches for operating a control circuit for supplying power to the heating element.

In devices for evaporating liquids in which a liquid is constantly supplied thereto for evaporation, care must be taken so that the evaporation of the liquid begins when the container has been supplied with a sufficient amount of liquid, as well as stopping evaporation when the entire amount of liquid has been evaporated. Control is thus necessary for the heating element by which the heating element can be connected and disconnected at times corresponding to such liquid levels.

A problem in the art is to provide such a control for a device for evaporating liquid which is simple and economic in operation and construction.

SUMMARY OF THE INVENTION

It is an object of the present invention to provide a device for controlling evaporation of a liquid which is simple and economic in operation and construction.

The above object is inventively achieved in a device having a liquid container having a heating element which is disposed on a base plate which is in turn supported by a leaf spring. The base plate has an end movable between two microswitches which are interconnected in a circuit for supplying power to the heating element.

A first microswitch disposed above the base plate is normally open, such as when no liquid is present in the container, and becomes closed for permitting supply of power to the heating element only when a pre-determined amount of liquid is supplied to the container and thus bends the leaf spring and allows the base plate to move away from the microswitch.

A second microswitch is disposed beneath the base plate and is normally closed and becomes open, thereby interrupting flow of power to the heating element, only when a sufficient amount of liquid is present to bend the leaf spring and the base plate attached thereto a sufficient amount to activate the second microswitch by the presence of too much liquid in the container.

For further safety monitoring of the evaporation device, the heating element may be provided with a temperature safety or monitoring device which temporarily interrupts flow of power to the heating element when the heating element is utilizing too much current and is thereby in danger of overheating.

DESCRIPTION OF THE PREFERRED EMBODIMENTS

Figure 1:
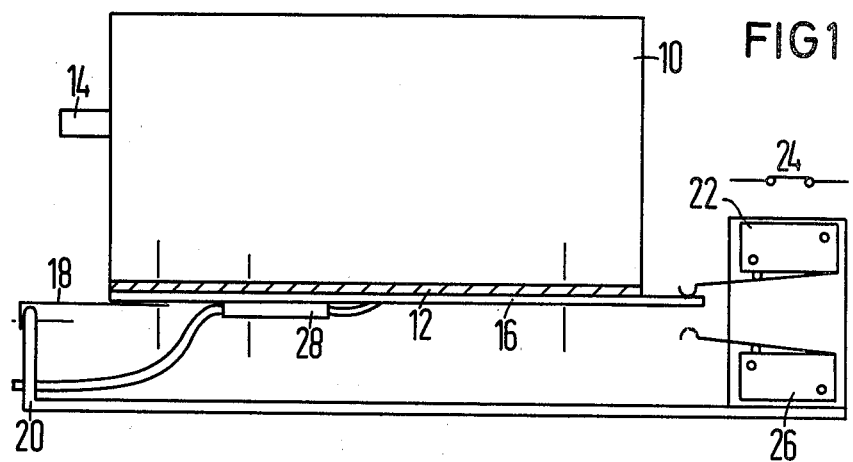
FIG. 1 is a side view of a device for controlling evaporation of a liquid constructed in accordance with the principles of the present invention.
Figure 2:
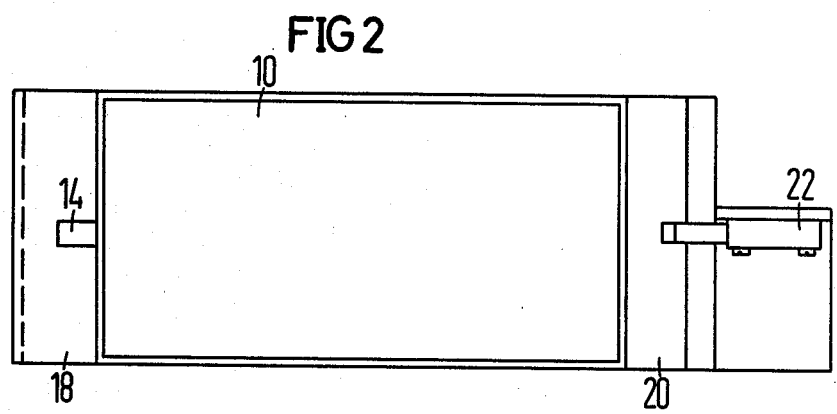
FIG. 2 is a plan elevational view of the device shown in FIG. 1.

As shown in FIGS. 1 and 2, a device for controlling evaporation of a liquid has a container 10 having a standard heating element 12 for elevating the temperature of liquid contained in the container 10 and evaporating same upon attainment of a suitable temperature of the liquid within the container 10. The container 10 is dimensioned in such a manner that the maximum accumulated liquid quantity is evaporated per unit of time without the necessity of completely emptying the container.

The container 10 is disposed on a base plate 16 which is attached at one end to a leaf spring 18 which is in turn connected to a support 20. The container 10 is thus entirely supported by the leaf spring 18, which will bend in an amount directly proportional to the amount of liquid in the container 10 at any given time.

At an opposite end of the base plate 16 are disposed a first microswitch 22 and a second microswitch 26. The first microswitch 22 is disposed so as to be in engagement with the base plate 16 when little or no liquid is in the container 10 and is in a normally open state when the base plate 16 is in such a position. As liquid is entered into the container 10 via the conduit 14, the base plate 16 moves downwardly against the bias of the leaf spring 18 as a result of the weight of the liquid and thereby moves out of engagement with the microswitch 22 which then changes to a closed state, allowing power to be supplied to the heating element 12. As power is supplied to the heating element 12, the temperature of the liquid in the container 10 is elevated and the liquid is evaporated.

Further monitoring of the device is undertaken by the second microswitch 26 disposed below the first microswitch 22 and which may also be engaged by the base plate 16. Under normal conditions, the microswitch 26 is not in engagement with the base plate 16 and is in a closed state. If, however, the liquid level in the container 10 rises, for example, because the incoming liquid can no longer be evaporated by the heating element 12, the container 10 will be lowered until the base plate 16 engages the microswitch 26 at which time the microswitch 26 is opened, thereby interrupting flow of power to the heating element 12, and ceasing the evaporating process. The bias of the leaf spring 18 is selected to correspond to the maximum amount of liquid desired to be in the container 10 which can be adequately evaporated by the heating element 12. The switch 26 may be activated, for example, if the heating element is for some reason not connected or is defective, or if too great a volume of liquid is supplied via the conduit 14, or if the microswitch 22 fails.

A further monitoring is undertaken by the interconnection of a temperature safety device 28 between the heating element 12 and a power supply. The temperature safety device 28 may be a compound bar or any other device known to those skilled in the art for switching between two states upon temperature dependence. The temperature safety device 28 interrupts flow of power to the heating element 12 if the heating element 12 is being heated too strongly and is therefore in danger of overheating. Again, such a situation may occur because the microswitch 22 for some reason fails to disconnect the heating element. This would allow interruption of power to the heating element 12 before the amount of liquid is supplied to the container 10 which is sufficient to activate the microswitch 26.

Figure 3:
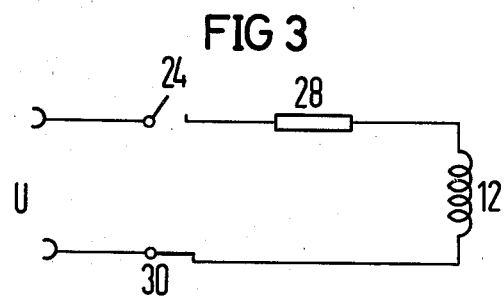
FIG. 3 is a circuit diagram for use in the device shown in FIG. 1.

A control circuit utilizing the above concept is shown in FIG. 3 wherein the heating element 12 is represented by a coil and is supplied with power at terminals across which a voltage U is connected. The contact 24 represents the contact for the microswitch 22, which is also shown in FIG. 1 in a normally closed state, and the contact 30 represents the contact for the microswitch 26. When the container 10 is empty, the contact 24 is open, while the contact 30 is closed. No current can flow through the heating element 12 in this condition. If the container 10 is supplied with liquid, the contact 24 is closed and current flows from the voltage source U through the contact 24, the temperature safety device 28, the heating element 12 and the contact 30. The heating element is functioning and the evaporation occurs. If an amount of liquid is supplied to the container 10 sufficient to bend the leaf spring 18 in an amount permitting engagement of the base plate 16 with the microswitch 26, the contact 30 is opened and again current flow to the heating element 12 is interrupted.

In the embodiment described above, the heating element 12 forms a base or bottom of the container 10. A heating plate may be utilized as the heating element 12 on which a separate container 10 is placed without departing from the inventive concept disclosed herein. The heating plate in such an embodiment may then serve as the base plate 16 for activating the microswitches 22 and 26.

Although other modifications and changes may be suggested by those skilled in the art it is the intention of the inventors to embody within the patent warranted hereon all changes and modifications as reasonably and properly come within the scope of their contribution to the art.

We claim as our invention:

1. A device for controlling evaporation of a liquid comprising:
    a container for receiving liquid to be evaporated;
    a heating element in contact with said container for heating liquid therein and evaporating said liquid;
    a base plate on which said container and heating element are disposed;
    a leaf spring interconnected between a support and said base plate for supporting said base plate at one end thereof and said container and permitting movement of an opposite free end of said base plate in response to an amount of liquid in said container;
    a normally closed microswitch disposed beneath said free end of base plate for interrupting flow of current to said heating element upon said container being supplied with an amount of liquid sufficient to move said free end of said base plate into engagement with said normally closed switch; and
    a normally open microswitch disposed above said free end of base plate and engaged therewith when no liquid is present in said container, whereby upon liquid being supplied to said container said free end of said base plate is moved out of engagement with said normally open microswitch closing said normally open microswitch and permitting flow of current to said heating element.

2. The device of claim 1 further comprising a temperature safety device for monitoring the temperature of said heating element interconnected between said heating element and a power supply.

3. The device of claim 1 wherein said heating element is contained in said base plate.

* * * * *